(12) United States Patent
Osher et al.

(10) Patent No.: US 11,096,823 B2
(45) Date of Patent: Aug. 24, 2021

(54) OPHTHALMIC MARKING DEVICE AND METHOD OF USING SAME

(71) Applicant: Beaver-Visitec International (US), Inc., Waltham, MA (US)

(72) Inventors: Robert H. Osher, Cincinnati, OH (US); Briana Rawson, Cambridge, MA (US); Collin Alexander Murray, Maynard, MA (US)

(73) Assignee: Beaver-Visitec International (US), Inc., Waltham, MA (US)

( * ) Notice: Subject to any disclaimer, the term of this patent is extended or adjusted under 35 U.S.C. 154(b) by 0 days.

(21) Appl. No.: 15/407,673

(22) Filed: Jan. 17, 2017

(65) Prior Publication Data

US 2017/0202705 A1 Jul. 20, 2017

Related U.S. Application Data

(60) Provisional application No. 62/278,634, filed on Jan. 14, 2016.

(51) Int. Cl.
*A61F 9/007* (2006.01)
*A61B 18/14* (2006.01)
(Continued)

(52) U.S. Cl.
CPC .......... *A61F 9/007* (2013.01); *A61B 18/1402* (2013.01); *A61F 9/0136* (2013.01);
(Continued)

(58) Field of Classification Search
CPC ....... A61F 2/1645; A61F 9/007; A61F 9/0079
See application file for complete search history.

(56) References Cited

U.S. PATENT DOCUMENTS 4,108,181 A * 8/1978 Saliaris .................. A61B 18/10
219/233
4,606,342 A 8/1986 Zamba et al.
(Continued)

FOREIGN PATENT DOCUMENTS

CN 2031272 U 1/1989
CN 2160371 Y 4/1994
(Continued)

OTHER PUBLICATIONS

"Contiguous," Cambridge Dictionaries, Sep. 27, 2015, <http://dictionary.cambridge.org:80/US/dictionary/english/contiguous>.*
(Continued)

*Primary Examiner* — Linda C Dvorak
*Assistant Examiner* — Ryan T Clark
(74) *Attorney, Agent, or Firm* — Budzyn IP Law, LLC

(57) ABSTRACT

An ophthalmic marking device is provided herein for marking a patient's eye. The device may include a handle and a tip with a tip element, a first portion of the tip element protruding from the tip to be exposed. The tip element is electrically conductive to resistively generate heat with electrical flow therethrough. A source of electrical power is associated with the device and electrically coupled to the tip element. The source of the electrical power and the tip element are configured to cause the first portion of the tip element to have a temperature in a range of 250° F.-450° F. Advantageously, the subject invention provides for a relatively low-cost device for marking a patient's eye and allows for creating a less traumatic marking on a patient's eye as compared to higher temperature electrocautery devices.

6 Claims, 4 Drawing Sheets

(51) Int. Cl.
   *A61F 9/013* (2006.01)
   *A61B 18/12* (2006.01)
   *A61F 2/16* (2006.01)
   *A61B 18/00* (2006.01)

(52) U.S. Cl.
   CPC .............. *A61B 2018/00178* (2013.01); *A61B 2018/126* (2013.01); *A61F 2/1645* (2015.04)

(56) References Cited

U.S. PATENT DOCUMENTS

| | | | |
|---|---|---|---|
| 4,674,499 A * | 6/1987 | Pao .................... | A61B 18/1402 604/20 |
| 4,907,587 A * | 3/1990 | Fedorov ................ | A61F 9/013 128/897 |
| 4,911,161 A | 3/1990 | Schechter | |
| 5,017,340 A | 5/1991 | Pribat et al. | |
| 5,688,265 A * | 11/1997 | Citronowicz ......... | A61B 18/10 219/233 |
| 5,920,883 A | 7/1999 | Tamaki et al. | |
| 6,925,333 B2 | 8/2005 | Krebs | |
| 7,070,596 B1 | 7/2006 | Woloszko et al. | |
| 7,862,563 B1 | 1/2011 | Cosman et al. | |
| 2002/0111608 A1 | 8/2002 | Baerveldt et al. | |
| 2005/0247692 A1* | 11/2005 | Axinte ................. | B23K 3/0307 219/240 |
| 2007/0088352 A1 | 4/2007 | Rosen | |
| 2008/0015565 A1 | 1/2008 | Davison | |
| 2008/0147058 A1 | 6/2008 | Horrell et al. | |
| 2009/0318846 A1* | 12/2009 | Prausnitz ........... | A61B 17/3203 604/20 |
| 2010/0076428 A1 | 3/2010 | Durgin et al. | |
| 2012/0053583 A1* | 3/2012 | Palanker .............. | A61B 18/042 606/45 |
| 2013/0023866 A1* | 1/2013 | Stringham ........... | A61B 18/082 606/29 |
| 2013/0096547 A1 | 4/2013 | Osher et al. | |
| 2013/0267787 A1* | 10/2013 | Warnock ................ | A61B 18/14 600/249 |
| 2014/0276751 A1* | 9/2014 | Sartor ................ | A61B 18/1402 606/33 |
| 2016/0206362 A1* | 7/2016 | Mehta ..................... | A61N 1/18 |

FOREIGN PATENT DOCUMENTS

| | | |
|---|---|---|
| CN | 2199763 Y | 6/1995 |
| CN | 102824213 A | 12/2012 |
| WO | 02056805 A1 | 7/2002 |

OTHER PUBLICATIONS

"Contiguous," Dictonary.com <http://www.dictionary.com/browse/contiguous>.*
McGraw-Hill Dictionary of Scientific & Technical Terms (2003), https://encyclopedia2.thefreedictionary.com/direct+voltage (last visited May 27, 2020).*
Beaver-Visitec International Inc.; XP-055049674; "Wet-Field Eraser"; Nov. 1, 2010; pp. 1-4; Waltham, MA, USA.
Robert H. Osher, MD. et al.; "Marking the Axis for a Toric IOL"; Mar. 2009; pp. 37-38, USA.
Robert H. Osher, MD.; "Iris fingerprinting: New method of improving accuracy in a toric lens orientation"; Cataract Refractive Surgery Today; vol. 36; Feb. 2010; pp. 351-352; USA.
Miyachi; Wire Gauge Sizes, AWG Wire Gauges; dated 2014.
Beaver-Visitec Internationa, Inc.; Accu-Temp Cautery brochure; dated 2011.
International Search Report and Written Opinion dated Apr. 10, 2017 from corresponding PCT Application No. PCT/US2017/013759.

* cited by examiner

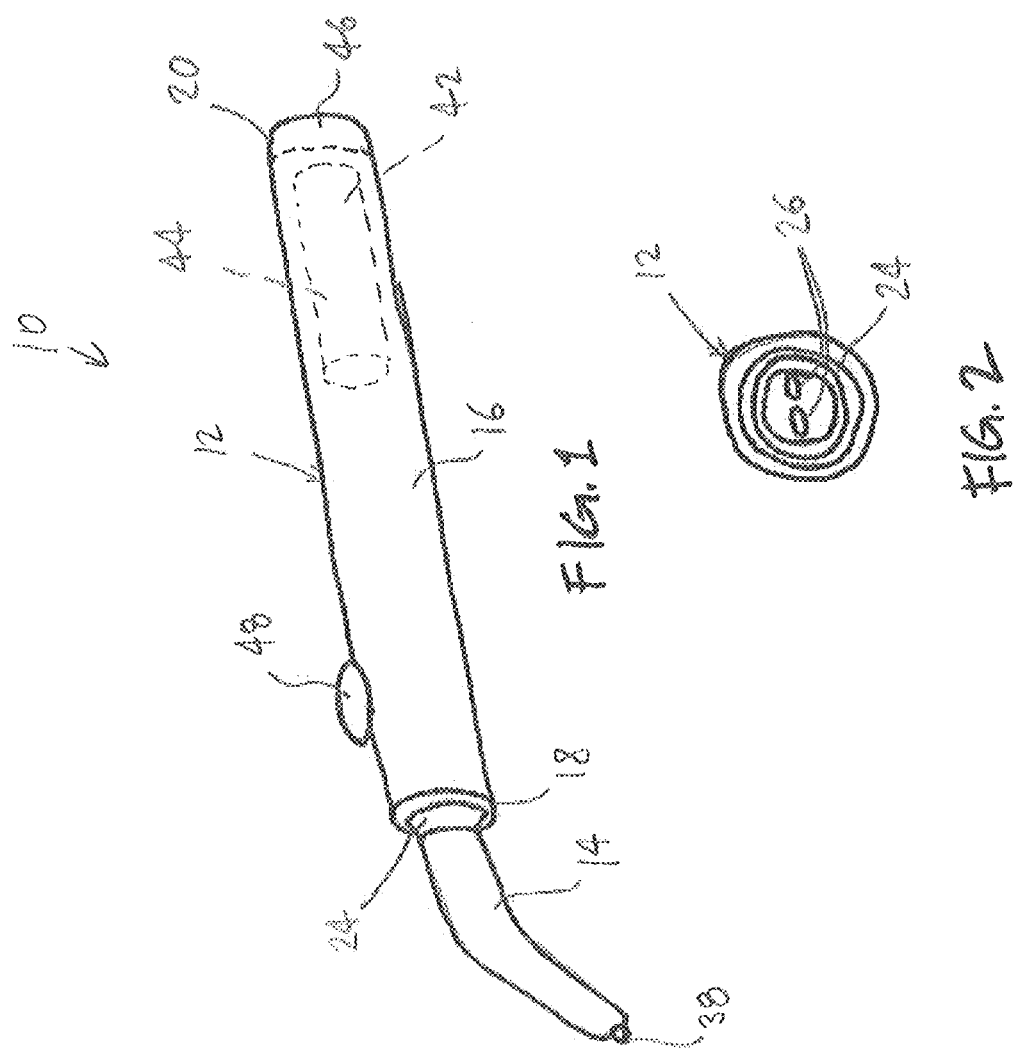

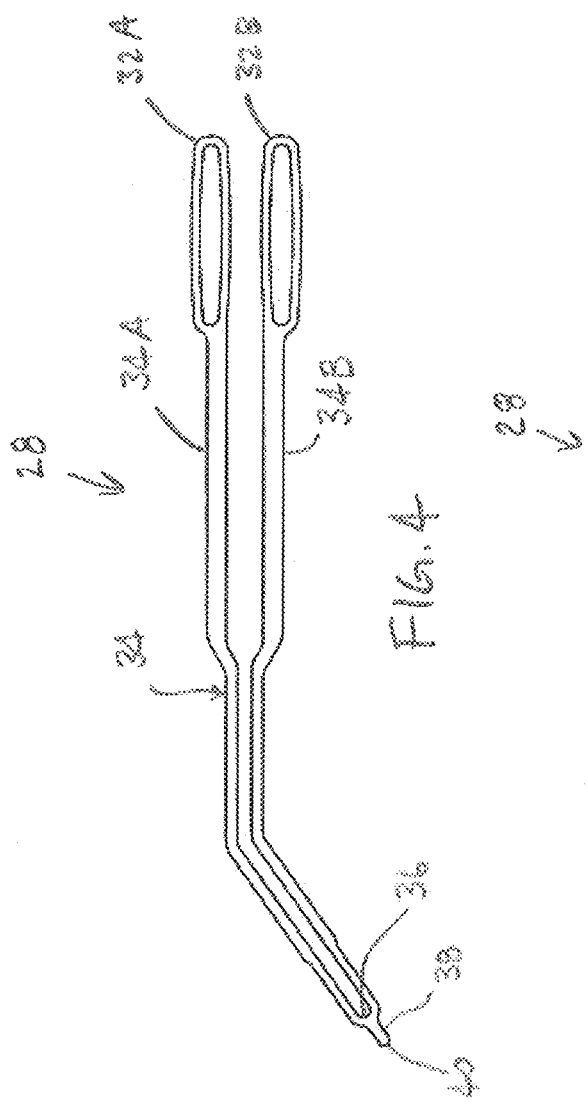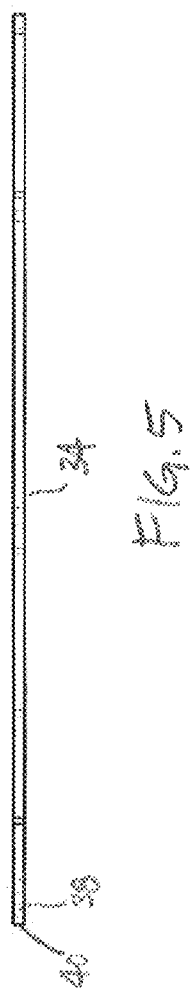

OPHTHALMIC MARKING DEVICE AND METHOD OF USING SAME

CROSS-REFERENCE TO RELATED APPLICATION

This application claims priority to U.S. Provisional Patent Application No. 62/278,634, filed Jan. 14, 2016, the contents of which are incorporated by reference herein.

BACKGROUND OF THE INVENTION

Methods and devices for marking a patient's eye are known in the prior art, particularly for making discernible reference marks on a patient's eye for use during surgery. For example, U.S. patent application Ser. No. 13/653,828, to the Assignee herein, discloses a method and device for marking a patient's eye before or during a surgical procedure, such as implantation of a toric lens. As disclosed therein, a bipolar electrocautery device may be utilized. Typical bipolar electrocautery devices are configured to generate high temperatures, often of about 900° F. and higher. These devices are generally tethered or otherwise connected to a remote power supply due to the need for a relatively high electrical input.

Cautery devices are known in the prior art which rely on electrical resistance heating, such as cautery devices sold under the brand "ACCU-TEMP" by Beaver-Visitec International, Inc. of Waltham, Mass., USA. As presently sold, these cautery devices are designed for fixed and variable temperature applications, rated for temperatures of 849° F. and higher.

SUMMARY OF THE INVENTION

An electrical resistance heating device is provided herein for marking a patient's eye. This device is particularly well-suited for marking a patient's eye in preparation for or during a surgical procedure where fixed reference marks on the patient's eye are required for a surgeon, such as during toric lens implantation. The device may include a body with a tip element secured to the body, a first portion of the tip element protruding from the body to be exposed. The tip element is electrically conductive to resistively generate heat with electrical flow therethrough. A source of electrical power is associated with the body and electrically coupled to the tip element. The source of the electrical power and the tip element are configured to cause the first portion of the tip element to have a temperature in a range of 250° F.-450° F. with electrical flow passing through the tip for 1-5 seconds. Advantageously, the subject invention provides for a lower-cost alternative to prior art devices for marking a patient's eye and allows for creating a less traumatic marking on the patient's eye as compared to the markings generated by higher temperature electrocautery devices.

These and other features of the invention will be better understood through a study of the following detailed description and accompanying drawings.

BRIEF DESCRIPTION OF THE DRAWINGS

FIG. 1 is a perspective view of a device formed in accordance with the subject invention;

FIG. 2 is a front elevational view of a handle useable with the subject invention;

FIGS. 4 and 5 show a tip element useable with the subject invention;

DETAILED DESCRIPTION

Figure 3:
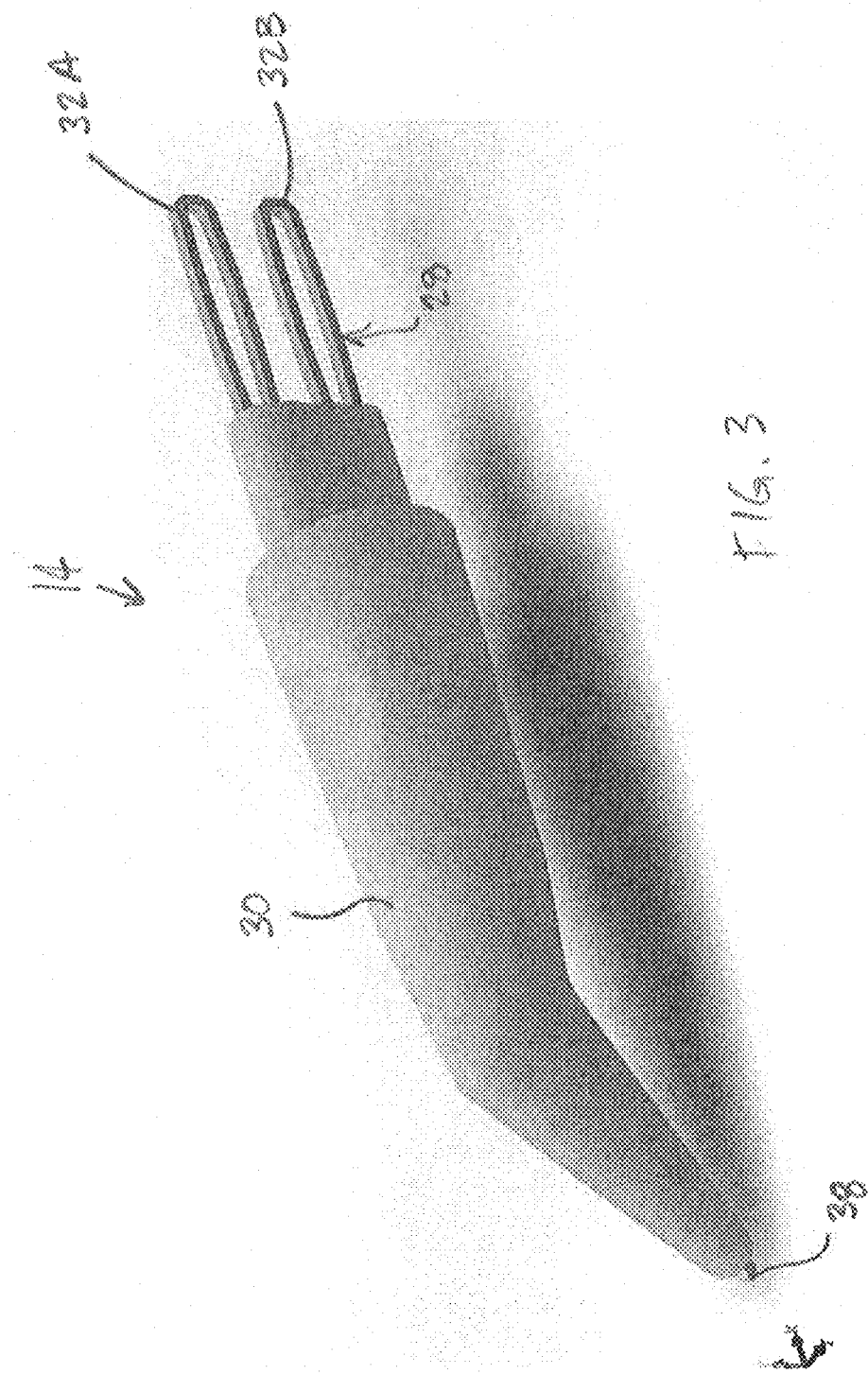
FIG. 3 is a perspective view of a tip useable with the subject invention.

With reference to FIG. 1, a device 10 is shown useable for making reference marks on an eye of a patient, particularly in preparation for or during a surgical procedure. The device 10 is particularly well-suited for cauterizing the tissue of a patient's eye to create discernible reference marks for a surgeon. The reference marks generally do not cause permanent damage and disappear with healing.

The device 10 includes a handle 12 to which is mounted a tip 14. Preferably, the tip 14 is removably mountable so as to permit re-use of the handle 12. The tip 14 is preferably provided in a sterilized condition for use. With removable mounting of the tip 14, sterilization of the handle 12 is avoided with re-use. It is possible to provide the device 10 as a single piece, with the tip 14 being permanently affixed to the handle 12. To permit re-use with this arrangement, sterilization of the exposed working area of the tip 14 has to be sterilized.

The handle 12 includes an enclosed body 16 with a distal end 18 and a proximal end 20. With the tip 14 being detachably mountable to the handle 12, a socket 22 is provided with the handle 12, preferably at the distal end 18, for mountingly receiving the tip 14. The socket 22 may include a ring 24 encircling one or more engageable electrical contacts 26. The socket 22 is configured to convey electrical power from the handle 12 to and from the tip 14.

With reference to FIGS. 3-5, the tip 14 includes a conductive tip element 28 which may be at least partially encompassed within insulative covering 30. With particular reference to FIG. 4, the tip element 28 includes two leads 32A, 32B with an arched conductor 34 extending therebetween. To avoid the shorting of electrical flow within the tip element 28, the leads 32A, 32B are provided spaced apart. In addition, the conductor 34 may be considered to include a supply side 34A and a return side 34B which are connected at apex 36. The conductor 34 is formed of an electrically conductive material so that the application of an electrical potential across the leads 32A, 32B results in electrical flow through the conductor 34. The tip element 28 is preferably a unitary element formed of a metallic material, more preferably, a stainless steel such as AISI 316 or AISI 316L. The tip element 28 may be stamped or etched from a blank material to be formed.

The covering 30, as shown in FIG. 3, may be provided to ensure that the supply side 34A and the return side 34B and the leads 32A, 32B of the conductor 34 remain in spaced relation. In addition, it is preferred that the covering 30 be formed of insulative materials to minimize electrical exposure to a user. Preferably, the covering 30 is formed of a polymeric material, more preferably, a polymeric material rated for relatively high temperatures, such as polycarbonate.

It is preferred that the covering 30 be provided on the tip 14 so that at least portions of the leads 32A, 32B be exposed and that a portion of the tip element 28 be also exposed.

With reference to FIG. 4, a protruding finger 38 may be provided on the conductor 34, for example coincident with the apex 36. As shown in FIG. 3, at least a portion of the finger 38 may be exposed by the covering 30 to allow for contact with the eye of a patient. Preferably, distal end 40 of the finger 38 is rounded to avoid sharp edges and corners.

It is preferred that the device 10 be provided as a self-contained, hand-held device which is not required to be tethered or otherwise connected to an additional piece of equipment or source of electrical power. Preferably, a battery or other electrical power storage 42 is associated with the handle 12, particularly being contained in a compartment 44 therein. A cover 46 may be provided, such as at the proximal end 20, to allow for access and replacement of the battery 42 as needed. The battery 42 need not be replaceable with the device 10 having a certain number of uses based on the life of the battery 42, with the device 10 and/or the handle 12 being disposed thereafter. The battery 42 may be rechargeable with a socket provided in the handle 12 for charging. Preferably, the battery 42 has a nominal voltage of at least 0.75 volts, more preferably, a nominal voltage in the range of 0.75-6 volts, more preferably, a nominal voltage in the range of 0.75-3 volts, more preferably, a nominal voltage of 1.5 volts. In addition, a switch 48 may be provided on the handle 12 which has a normally-open state. The switch 48 may be biased to the normally-open state, such as by spring biasing. The switch 48 may be adjustable, such as by being pressed or slid, to a closed state, where the switch 48 causes a corresponding circuit to be activated.

As shown in FIG. 2, the contacts 26 may be formed to receive the leads 32A, 32B in spaced relation. The contacts 26 may be configured to insertingly receive the leads 32A, 32B with sufficient interengagement to allow for electrical conduction therebetween and retention of the tip 14 by the handle 12. The tip 14 may be removed by withdrawing the leads 32A, 32B from the contacts 26.

Figure 6:
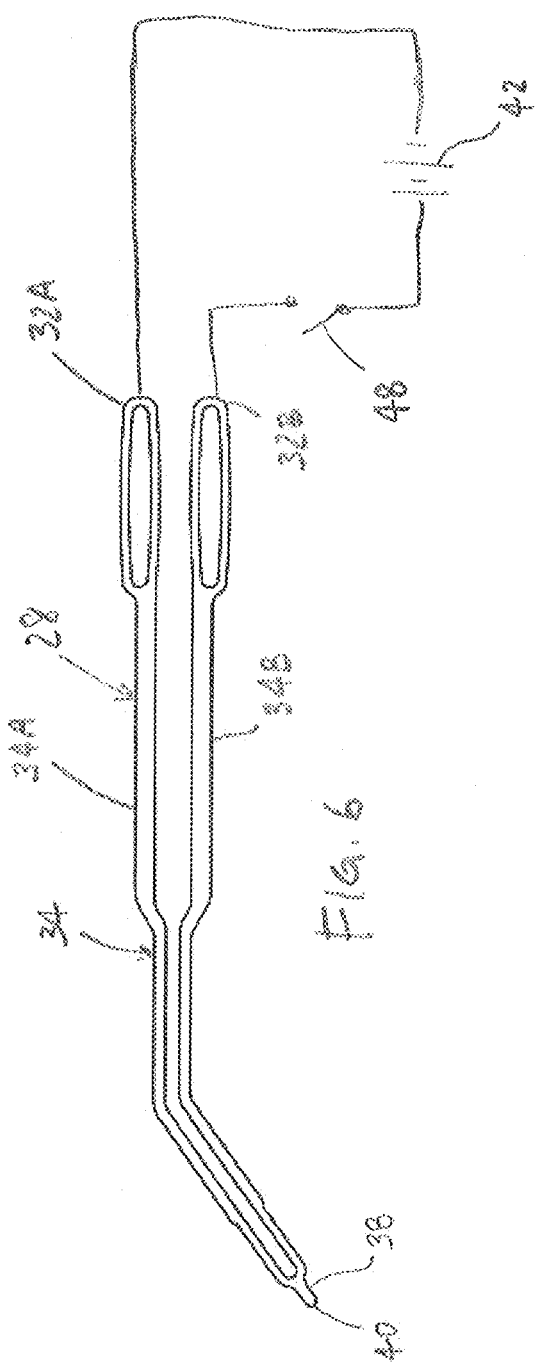
FIG. 6 is an electrical schematic of an embodiment of the subject invention.

With reference to FIG. 6, a schematic of an electrical circuit useable with the device 10 is shown. The battery 42 is electrically connected to the leads 32A, 32B using any known wiring and connectors, which may be provided in the handle 12. The switch 48 is shown in its normally open state. With the closing of the switch 48, electrical flow from the battery 42 is caused to pass through the tip element 28.

The tip element 28 is configured to resistively generate heat with electrical flow therethrough. With the battery being nominally rated for 1.5 volts, and with the tip element 28 being formed of AISI 316 stainless steel, a temperature of at least 250° F. can be expected at the distal end 40 of the finger 38 with the switch 48 being in a closed state for a minimum of three seconds.

A temperature in the range of 250° F.-450° F. in the tip element 28, particularly at the finger 38, with the closing of the switch 48 for about 1-5 seconds is desired in the device 10. The configuration, including the material, of the tip element 28 and the voltage of the battery 42 may be varied to provide these parameters. With a working range of 250° F.-450° F., it has been found that sufficient heat may be applied to make discernible reference marks on the eye of a patient, particularly with contact between the finger 38 and the patient's eye for at least one second. It is preferred that a surgeon close the switch 48 prior to contact with the patient's eye to allow the tip element 28 to be pre-heated in the range of 250° F.-450° F. before contact; once heated, contact by the tip element 28, e.g., the finger 38, with the patient's eye for at least one second should result in the creation of a discernible reference mark.

Heat is resistively generated with electrical flow. Generally, the longer the switch 48 is closed, the higher the temperature at the finger 38 will be, subject to a maximum achievable temperature. Heat beyond 450° F. also causes cauterization of the tissue, but may not be required. In addition, with the relatively simple circuitry of the device 10, high voltages are not required to be accommodated for with the device 10, thereby limiting manufacturing costs.

Figure 7:
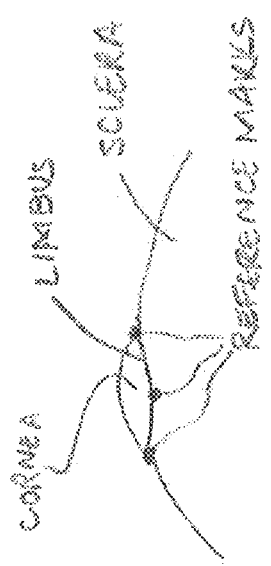
FIG. 7 is a representation of reference marks which may be formed on a patient's eye with the subject invention.

With reference to FIG. 7, discernible reference marks may be formed in or near the limbus of a patient's eye, particularly with reference to procedures related to the cornea, such as toric lens implantation. These reference marks may be spaced apart about the cornea as polar coordinates, such as north, south, east and west markings. With the device 10, a user can cause the reference marks to be made by pressing the finger 38 at a target site, and maintaining contact to allow for a temperature in the range of 250° F.-450° F. to be applied to the patient's eye for at least one second.

What is claimed is:

1. A method of marking a patient's eye with reference marks for ophthalmic procedures, the method comprising:
    providing an ophthalmic marking device having:
        a handle having an enclosed body with a proximal end and a distal end with first and second contacts exposed therethrough;
        a tip removably mountable to said distal end of said enclosed body of said handle;
        an electrically conductive tip element at least partially within said tip, said tip element including spaced-apart first and second leads with an arched conductor extending therebetween in physical-direct contact with said first and second leads to define a closed electrical flow path between said first and second leads such that application of an electrical potential across said first and second leads results in electrical flow through said conductor, a first portion of said tip element protruding from said tip to be exposed, wherein said first and second contacts are configured to insertingly receive said first and second leads, and wherein said first and second leads each include a loop-shaped portion, said loop-shaped portions being received in said first and second contacts with sufficient interengagement therebetween to retain said conductive tip on said handle when mounted thereto; and,
        an electrical power storage contained within the enclosed body, said electrical power storage being electrically connectable to said conductive tip element with said first and second leads received in said first and second contacts, respectively, with said tip removably mounted to said enclosed body, wherein, removal of said tip from enclosed body causes separation of said first and second leads from said first and second contacts,
        wherein, said tip element and said electrical power storage are configured so that, with electrical flow through said tip element caused by said electrical power storage, heat is resistively generated in said tip element with temperature in the range of 250° F.-450° F. at said first portion of said tip element;
    actuating said ophthalmic marking device to allow said electrical power storage to cause electrical flow through said tip element so that heat is resistively generated in said tip element with a temperature in the range of 250° F.-450° F. at said first portion of said tip element; and,
    contacting a target site on a patient's eye to be marked with a reference mark with said first portion of said tip element and maintaining contact for at least one second with the temperature at said first portion of said tip element being in the range of 250° F.-450° F.

2. A method as in claim 1, wherein said actuating is initiated prior to contacting the target site.

3. A method as in claim 1, wherein said electrical power storage is a battery having a voltage of at least 0.75 volts.

4. A method as in claim 1, wherein said electrical power storage has a voltage of 0.75-6.0 volts.

5. A method as in claim 4, wherein said electrical power storage has a voltage of 0.75-3.0 volts.

6. A method as in claim 5, wherein said electrical power storage has a voltage of 1.5 volts.

\* \* \* \* \*